(12) United States Patent
Lattner et al.

(10) Patent No.: US 10,196,571 B2
(45) Date of Patent: Feb. 5, 2019

(54) CONVERSION OF LIGNIN TO FUELS AND AROMATICS

(71) Applicant: ExxonMobil Chemical Patents Inc., Baytown, TX (US)

(72) Inventors: James R. Lattner, LaPorte, TX (US); Teng Xu, Houston, TX (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 184 days.

(21) Appl. No.: 14/876,940

(22) Filed: Oct. 7, 2015

(65) Prior Publication Data

US 2016/0145497 A1    May 26, 2016

Related U.S. Application Data

(60) Provisional application No. 62/082,196, filed on Nov. 20, 2014.

(51) Int. Cl.

| | |
|---|---|
| *C10G 1/02* | (2006.01) |
| *C10G 3/00* | (2006.01) |
| *C07C 2/86* | (2006.01) |
| *C07C 4/14* | (2006.01) |
| *C10G 1/00* | (2006.01) |

(Continued)

(52) U.S. Cl.
CPC ............... *C10G 1/02* (2013.01); *C07C 2/864* (2013.01); *C07C 4/14* (2013.01); *C10G 1/002* (2013.01); *C10G 3/42* (2013.01); *C10G 3/50* (2013.01); *C10K 1/16* (2013.01); *C10K 1/18* (2013.01); *C10B 49/22* (2013.01); *C10B 53/02* (2013.01); *C10G 2300/1014* (2013.01); *C10G 2300/44* (2013.01); *Y02P 30/20* (2015.11)

(58) Field of Classification Search
None
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu |

(Continued)

FOREIGN PATENT DOCUMENTS

| | | |
|---|---|---|
| WO | 94/15896 | 7/1994 |
| WO | 2006/119357 | 11/2006 |

OTHER PUBLICATIONS

Brown, "Advanced Biofuels: Back to Fundamentsls", presentation at the Biomass Education Field Day, Nov. 16-18, 2010, Knoxville, TN, pp. 1-30.

(Continued)

*Primary Examiner* — Philip Y Louie

(57) ABSTRACT

Methods are provided for converting lignin-containing biomass into compounds that are more readily processed to form fuel and/or chemical products. The methods can allow for removal of at least a portion of the oxygen in lignin, either during or after depolymerization of lignin to single ring aromatic compounds, while optionally reducing or minimizing aromatic saturation performed on the aromatic compounds. The methods can include use of quench solvent to control reactions within the product stream from a pyrolysis process and/or use of a solvent to assist with hydroprocessing of lignin, lignin-containing biomass, or a pyrolysis oil.

15 Claims, 4 Drawing Sheets

(51) Int. Cl.
*C10K 1/16* (2006.01)
*C10K 1/18* (2006.01)
C10B 49/22 (2006.01)
C10B 53/02 (2006.01)

(56) References Cited

U.S. PATENT DOCUMENTS

| | | | |
|---|---|---|---|
| 3,832,449 | A | 8/1974 | Rosinski et al. |
| 4,016,218 | A | 4/1977 | Haag et al. |
| 4,016,245 | A | 4/1977 | Plank et al. |
| 4,076,842 | A | 2/1978 | Plank et al. |
| 4,320,242 | A * | 3/1982 | Onodera ............ C07C 4/18 208/111.15 |
| 4,375,573 | A | 3/1983 | Young |
| 6,596,908 | B1 * | 7/2003 | Hermescec .......... C07D 307/44 162/47 |
| 8,202,332 | B2 | 6/2012 | Agblevor |
| 8,293,952 | B2 | 10/2012 | Levin |
| 8,344,197 | B2 | 1/2013 | Lattner et al. |
| 2003/0100807 | A1 | 5/2003 | Shabtai et al. |
| 2003/0115792 | A1 | 6/2003 | Shabtai et al. |
| 2008/0050792 | A1 | 2/2008 | Zmierczak et al. |
| 2009/0151253 | A1 | 6/2009 | Manzer et al. |
| 2010/0137663 | A1 | 6/2010 | Chen et al. |
| 2011/0092755 | A1 | 4/2011 | Lattner et al. |
| 2011/0275868 | A1 | 11/2011 | Prochazka et al. |
| 2011/0315537 | A1 * | 12/2011 | Daugaard ............ B01D 5/0027 201/19 |
| 2012/0167452 | A1 * | 7/2012 | Platon ................ B01D 53/1487 44/307 |
| 2012/0203042 | A1 | 8/2012 | Huber et al. |
| 2013/0025191 | A1 * | 1/2013 | Chen ...................... C10L 1/023 44/451 |
| 2013/0152454 | A1 | 6/2013 | Baird et al. |
| 2013/0158329 | A1 | 6/2013 | Brandvold |
| 2013/0232853 | A1 * | 9/2013 | Peterson ................ C07G 1/00 44/307 |

OTHER PUBLICATIONS

Patwardhan et al., "Understanding the Fast Pyrolysis of Lignin", ChemSusChem, 2011, vol. 4, pp. 1629-1636.

* cited by examiner

CONVERSION OF LIGNIN TO FUELS AND AROMATICS

CROSS REFERENCE TO RELATED APPLICATIONS

This application claims priority to and the benefit of U.S. Provisional Application Ser. No. 62/082,196, filed Nov. 20, 2014, which is incorporated herein by reference.

FIELD OF THE INVENTION

Methods are provided for conversion of lignin into fuels and/or aromatic compounds.

BACKGROUND OF THE INVENTION

In an effort to reduce greenhouse gas emissions, various research efforts have been devoted to developing technologies to produce fuels and chemical products from renewable resources. Some types of biomass materials that could be valuable for fuel and chemical product production are lignin-containing materials, which can include woody biomass or other biomass containing lignocellulose. Lignocellulose can be used directly as a type of biomass, or a digestion process can be used to separate cellulose from a lignin-containing portion. Various pyrolysis, catalytic pyrolysis, and catalytic fast pyrolysis methods have been proposed for converting lignocellulose and/or lignin-containing materials to compounds that can be more readily converted into desired products. Unfortunately, lignin-containing materials remain a difficult source of biomass to use effectively for production of renewable fuel and chemical products.

U.S. Patent Application Publication No. 2012/0203042 describes methods for pyrolyzing a hydrocarbonaceous feed to produce pyrolysis products. The various methods include using recycle of olefins generated during pyrolysis back to the pyrolysis reaction zone to alter the product composition. The methods also include using variations in pyrolysis temperature and/or catalysts to modify the pyrolysis products.

U.S. Patent Application Publication No. 2011/0275868 describes methods for converting lignin-containing starting materials into a pyrolysis gas, dealkylating the pyrolysis gas, and then separating aromatics of a desired boiling range from the dealkylated pyrolysis gas. The dealkylation process is described as a hydrodealkylation or steam dealkylation in the presence of hydrogen or water. The dealkylation is performed without allowing substantial cooling of the pyrolysis gas relative to the exit temperature of the pyrolysis gas from the pyrolysis process.

U.S. Patent Application Publication No. 2003/0115792 describes methods for converting lignins into a high octane blending component. Lignin is depolymerized using a base catalyzed process, followed by hydroprocessing of the depolymerized lignin to form $C_7$-$C_{10}$ alkylbenzenes.

U.S. Patent Application Publication No. 2010/0137663 describes methods for hydrogenation and base catalyzed depolymerization for lignin conversion. In an initial step, lignin is hydrogenated to convert aromatics to saturated compounds and to remove some oxygen. This reduces the acidity of the hydrogenated lignin compounds, allowing a lower strength base to be used for base catalyzed depolymerization.

U.S. Patent Application Publication No. 2009/0151253 discloses methods and systems to convert carbonaceous materials (such as biomass) into synthesis gas and other downstream products (such as alcohols). In certain embodiments, pyrolysis is performed in the presence of a catalyst such as heterogeneous catalysts (such as $SiO_2$—$Al_2O_3$, $Pt/SiO_2$—$Al_2O_3$, $WO_x/ZrO_2$, $SO_x/ZrO_2$), zeolites (such as HY-zeolite, alpha-zeolite, HZSM-5, ZSM-5, or klinoptilolite), acid catalysts, clay catalysts (e.g., acidified or activated clay catalysts), Al-MCM-41 type mesoporous catalysts, activated alumina, CoMo catalysts, and Ni/Al co-precipitated catalysts. In some embodiments, a cation such as $K^+$, $Li^+$, or $Ca^{2+}$ can be used to increase the selectivity and yield of char and/or to lower the selectivity and yield of tar during pyrolysis.

U.S. Pat. No. 8,202,332 discloses processes for fractional catalytic pyrolysis of biomass materials. The processes involve the use of a suitable catalyst in a fluidized bed pyrolysis system. Suitable catalysts are described as including H-ZSM-5, an aluminosilicate zeolite catalyst, and super acid catalysts, such as sulfated zirconia super acid catalysts.

U.S. Pat. No. 8,293,952 describes the production of pyrolysis products having a greater stability than pyrolysis products obtained from conventional pyrolysis production processes by using a basic metal oxide catalyst, such as a Group 2, Group 3, or Group 4 metal from the IUPAC Periodic Table of Elements.

U.S. Pat. No. 8,344,197 describes systems and methods for production of xylenes, including para-xylene, by methylation of benzene and toluene in the presence of methanol and a suitable molecular sieve.

It is desirable to improve the quality of bio-oil produced from lignin-containing feedstocks and provide a method for producing aromatics, particularly para-xylene, from lignin.

SUMMARY OF THE INVENTION

The present invention provides methods of converting lignin to aromatic compounds, particularly para-xylene. In one aspect, a lignin-containing feed is processed under effective depolymerization conditions to form a depolymerized effluent containing monolignols, which is mixed with a solvent to form a mixture of depolymerized effluent and solvent. The solvent, which reduces the concentration of reactive compounds in the depolymerization effluent, preferably has a T5 boiling point of at least about 240° C. and contains at least about 50 wt % of aromatic compounds. The mixture of at least a portion of the depolymerized effluent and solvent is then exposed to a deoxygenation catalyst under effective deoxygenation conditions to form a deoxygenated effluent containing aromatic compounds.

In another aspect, a lignin-containing feed is processed under effective depolymerization conditions to form a depolymerized effluent containing monolignols, of which at least a portion thereof is exposed to a deoxygenation catalyst under effective deoxygenation conditions to form a deoxygenated effluent containing alkylated benzene compounds. At least a portion of the alkylated benzene compounds is exposed to a dealkylation catalyst under effective dealkylation conditions to form benzene, and at least a portion of the benzene is then exposed to an alkylation catalyst and methanol under effective alkylation conditions to form xylene.

In still another aspect, a lignin-containing feed and a solvent are exposed to a deoxygenation catalyst under effective deoxygenation conditions to form a deoxygenated effluent having an aromatics content of at least about 25 wt %. At least a first portion of the deoxygenated effluent is exposed to a dealkylation catalyst under effective dealkylation conditions to form benzene, and at least a portion of the benzene is then exposed to an alkylation catalyst and methanol under effective alkylation conditions to form xylene.

DETAILED DESCRIPTION OF THE EMBODIMENTS

Overview

Figure 1:
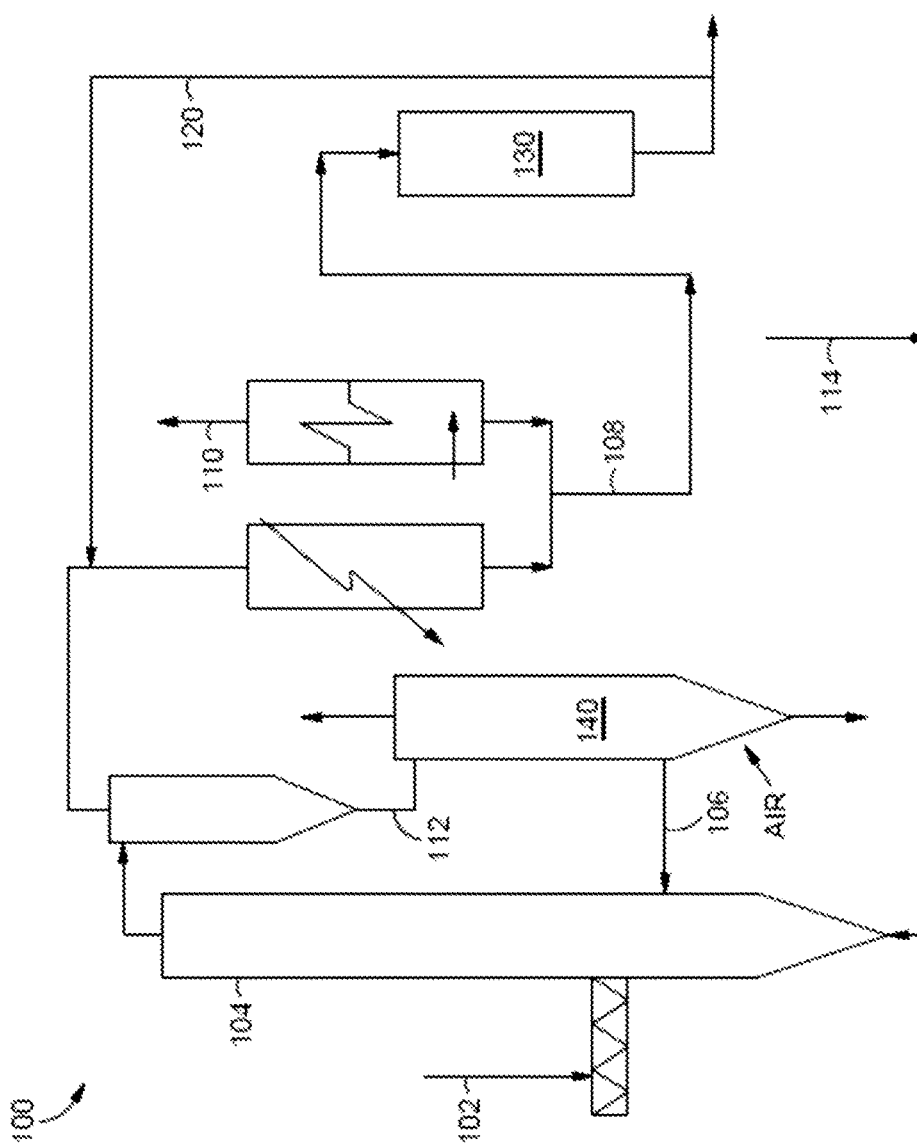
FIG. 1 schematically shows an example of a reaction system for mixing a pyrolysis effluent with a quench solvent.

Lignin compounds are polymeric compounds with monomeric units that include both aromatic rings and oxygen-containing functional groups. The aromatic rings in lignin are individual rings (as opposed to multiple fused rings), which make the aromatic rings in lignin potentially attractive as a feed source for forming naphtha boiling range fuels and/or various aromatic chemicals, such as para-xylene. However, the substantial oxygen content in lignin can present difficulties in converting lignin into desired fuel and/or chemical products.

In various aspects, systems and methods are provided for converting lignin-containing biomass into compounds that are more readily processed to form fuel and/or chemical products. The systems and methods can allow for removal of at least a portion of the oxygen in lignin, either during or after depolymerization of lignin to single ring aromatic compounds, while optionally reducing or minimizing aromatic saturation performed on the aromatic compounds. In this description, it is understood that pyrolysis of a lignin-containing feed corresponds to a higher severity type of depolymerization. Some methods can include use of quench solvent to control reactions within the product stream from a pyrolysis process. Additionally or alternately, some methods can include use of a solvent to assist with hydroprocessing of lignin, lignin-containing biomass, and/or a pyrolysis oil derived from lignin-containing biomass, such as a pyrolysis oil formed while using a quench solvent after pyrolysis. Additionally or alternately, mono-lignol compounds formed from pyrolysis or hydroprocessing of lignin-containing material can be further processed to form desired aromatic compounds, optionally including formation of para-xylene.

Processing of Lignin—Pyrolysis with Quenching of Pyrolysis Effluent

Pyrolysis of a biomass feed, such as a lignin-containing biomass feed, can typically result in formation of a pyrolysis oil effluent containing a variety of compounds. The effluent from pyrolysis can include a gas phase effluent portion, a liquid effluent portion, and/or a solid product portion. Due to the high temperatures used in a pyrolysis process, the majority of the products from pyrolysis can be part of the gas phase effluent. The liquid effluent portion and any solid product portion represent lower value products. A portion of these lower value products may be suitable for recycle to the pyrolysis reaction. Otherwise, these lower value products can be handled in a manner similar to coke, where the products may be burned or otherwise processed simply for removal from the system. The oxygen content of the gas phase pyrolysis oil effluent can be greater than 1 wt %, such as at least about 5 wt % and optionally up to about 10 wt % or more. The oxygen-containing compounds in a pyrolysis oil can include a variety of unsaturated and/or aromatic compounds. In conventional processes, the gas phase effluent from pyrolysis is subsequently "condensed" by reducing the temperature of the effluent. This can result in production of a liquid pyrolysis oil product from the gas phase pyrolysis effluent.

Without being bound by any particular theory, it is believed that at least a portion of the gas phase effluent from a biomass pyrolysis process corresponds to "monomers" derived from lignin compounds in the biomass feed. These monomers can include, for example, single ring aromatic alcohols (lignols), such as p-coumaryl alcohol, coniferyl alcohol, and sinapyl alcohol. The monomers can also include other carboxylic acids, alcohols, aldehydes, and/or other compounds that may be reactive under the conditions present at the exit from a reactor performing a pyrolysis reaction.

Figure 2:
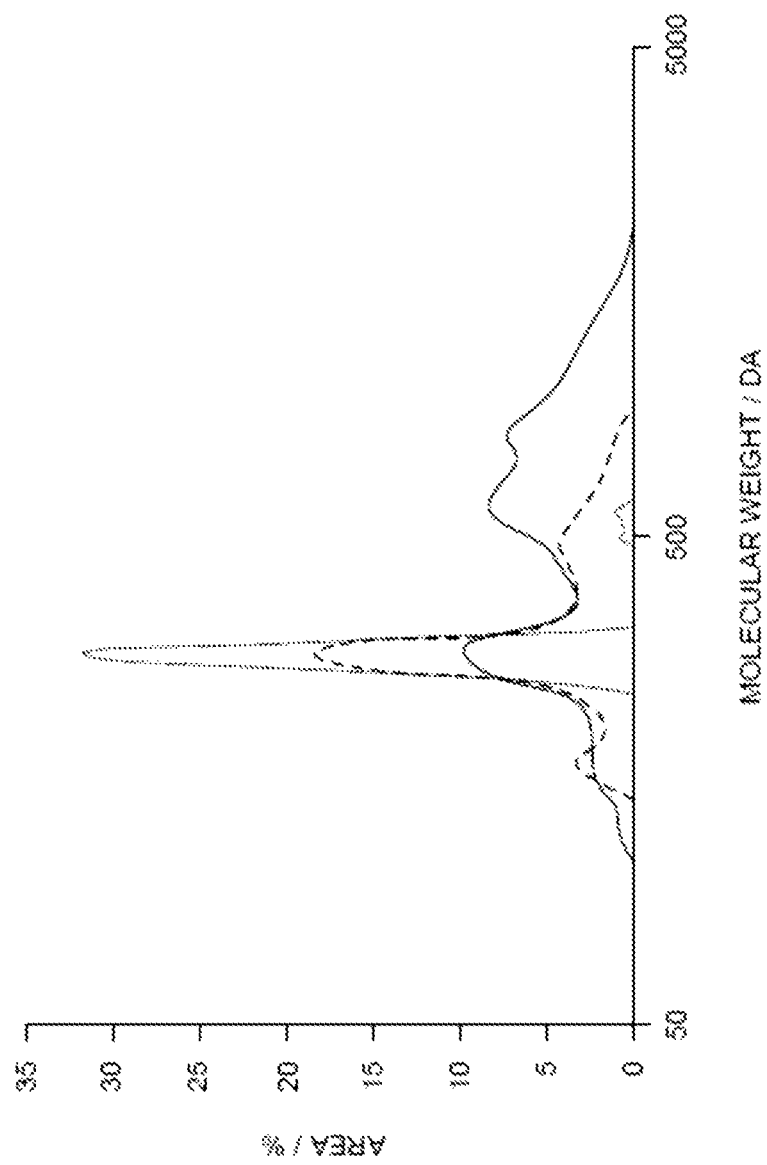
FIG. 2 shows an example of an effluent from a pyrolysis reaction prior to cooling or condensing the effluent.
Figure 3:
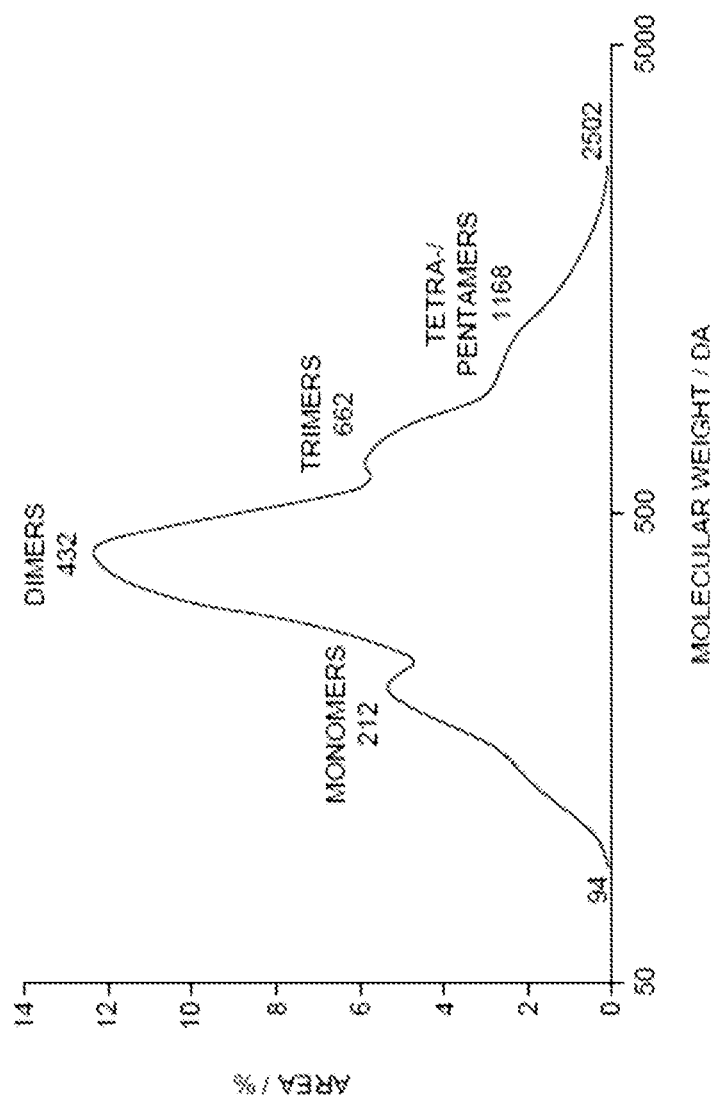
FIG. 3 shows an example of an effluent from a pyrolysis reaction after condensation of the effluent.

FIG. 2 shows an example of a molecular weight distribution for a pyrolysis oil derived from a lignin feed, as reported in a literature reference. (See "Understanding the Fast Pyrolysis of Lignin," Patwardhan, Brown, and Shanks, Chem Sus Chem Vol. 4, No. 11, 1629-1636.) In FIG. 2, the dashed line corresponds to the molecular weight distribution (in Daltons) for a pyrolysis oil that was measured prior to any cooling or other condensation of the effluent. It is noted that the molecular weight on the horizontal axis in FIG. 2 is shown on a log scale. As shown in FIG. 2, the molecular weight distribution for the pyrolysis oil prior to cooling and/or condensation appears to have a single dominant peak at a molecular weight between 200 and 300 Da, indicating that most of the pyrolysis oil corresponds to monomer type units having a similar molecular weight. This is in contrast to the molecular weight distribution in FIG. 3 which shows the molecular weight distribution (in Daltons) for a pyrolysis oil after condensation of vapors to recover a liquid product. The molecular weight distribution in FIG. 3 is also shown on a log scale. In the molecular weight distribution in FIG. 3, the largest peak in the distribution corresponds to a "dimer" of units from the pyrolysis effluent.

The molecular weight distributions in FIGS. 2 and 3 demonstrate that the products from a pyrolysis process can be modified during the condensation of the pyrolysis effluent to a liquid state. In addition to forming dimers, the distribution in FIG. 3 indicates that other still larger compounds can also be formed. Without being bound by any particular theory, it is believed that the formation of dimers and larger compounds in a condensed pyrolysis oil contributes to the difficulty in processing pyrolysis oils under conventional hydroprocessing conditions.

In various aspects, the formation of higher molecular weight compounds in a pyrolysis oil can be reduced or minimized by combining the pyrolysis oil with a quench solvent prior to substantial cooling of the pyrolysis oil. The effluent generated by a pyrolysis reaction can exit the reaction zone for pyrolysis at an exit temperature. In various aspects, mixing the pyrolysis oil effluent with the quench solvent prior to substantial cooling can correspond to mixing the pyrolysis oil effluent with the quench solvent at a mixing temperature that differs from the exit temperature of the pyrolysis oil effluent from a pyrolysis reaction zone by about 100° C. or less, or about 75° C. or less, or about 50° C. or less. It is noted that the case of the pyrolysis effluent being the same temperature when exiting the pyrolysis reaction zone and at mixing is defined to be included within having a temperature that differs by less than a threshold amount. The quench solvent may be at a substantially lower temperature during mixing such as more than 100° C. different from the mixing temperature, or the quench solvent may be heated to a temperature similar to the pyrolysis effluent, such as a temperature that differs from the pyrolysis effluent temperature by about 100° C. or less, or 75° C. or less, or 50° C. or less. It is noted that the case of the quench solvent being the same temperature as the pyrolysis effluent when the quench solvent is mixed with the pyrolysis oil is defined to be included within having a temperature that differs by less than a threshold amount.

The quench solvent can be added to the pyrolysis oil in an amount sufficient to reduce the concentration of reactive components within the pyrolysis oil. This can reduce the reaction rate of the reactive components. Additionally, in some aspects the quench solvent can rapidly reduce the temperature of the pyrolysis oil exiting from the pyrolysis reaction zone. This can reduce or minimize the amount of time the pyrolysis oil spends at temperatures suitable for formation of larger molecules.

The effluent from the pyrolysis process can be mixed with the quench solvent by any convenient method. One option can be to pass the pyrolysis effluent into the quench solvent by bubbling the pyrolysis gas through the quench solvent, with the quench solvent being at a temperature where the quench solvent is a liquid. Another option can be to heat the quench solvent to a temperature where the quench solvent is a gas, mix the quench solvent with the gas phase pyrolysis effluent, and then cool the mixture.

In various aspects, the quench solvent can be selected to have a variety of characteristics. One preferred characteristic is to have a quench solvent with a boiling point (or alternatively a T5 boiling point) of at least about 240° C., such as at least about 250° C., or at least about 275° C. A high boiling point for the quench solvent can be beneficial so that the quench solvent will tend to form a condensed phase at a temperature similar to or greater than the temperature at which the gas phase pyrolysis oil effluent tends to form a condensed phase. Another preferred characteristic is to have a quench solvent with a substantial aromatic content, such as a composition where at least about 50 wt % of the quench solvent corresponds to aromatic (including phenolic) compounds, such as at least 60 wt %. A high aromatic content can be beneficial for allowing the pyrolysis effluent to be soluble in the quench solvent. Still another preferred characteristic is to have a quench solvent that is substantially free of vinyl or other allylic functional groups, such as about 5 wt % or less of compounds containing vinyl or allylic functional groups, preferably about 3 wt % or less, or more preferably about 1 wt % or less. Without being bound by any particular theory, it is believed that vinyl and/or allylic functional groups can contribute to the formation of larger compounds during a conventional condensation of the gas phase portion of a pyrolysis oil effluent. Using a quench solvent that contains vinyl and/or allylic functional groups would reduce the value of the quench solvent for diluting the pyrolysis oil, as the quench oil itself might provide a source of molecules that can polymerize to form larger compounds. Yet another preferred characteristic is to use a sufficient amount of the quench solvent. For example, when mixing the gas phase pyrolysis oil effluent with the quench oil, the resulting mixture can contain at least about 50 wt % of the quench solvent, such as at least about 60 wt %, or at least about 70 wt %.

One suitable source for a quench solvent for mixing with the gas phase effluent portion of a pyrolysis process can be to use a hydrotreated portion of the resulting gas phase pyrolysis effluent. A hydrotreatment process can be used to reduce the oxygen content of a pyrolysis effluent to a desired level, such as about 1 wt % or less. Such a hydrotreatment can also be sufficient to reduce or minimize the number of vinyl or allylic functional groups in the condensed pyrolysis oil. As a result, a portion of hydrotreated condensed pyrolysis oil having a suitable boiling range, such as a T5 boiling point of at least about 240° C., can be used as the quench solvent, as such a hydrotreated pyrolysis oil can have a relatively low activity when mixed with fresh gas phase effluent from a pyrolysis process.

FIG. 1 schematically illustrates an example of a configuration 100 of a pyrolysis reactor suitable for producing pyrolysis bio-oil. As will be discussed in greater detail herein, bio-oil 108 can be produced from pyrolysis of biomass 102, such as wood chips or corn stover. Depending on the source, bio-oil 108 can be a complex mixture of organic oxygenates, characterized by high oxygen content (>35%), reactive oxygen functional groups, thermal instability, corrosivity, low energy content and a significant water fraction (10-20%), making it unsuitable for use as a refinery feedstock or transportation fuel without significant further upgrading. In FIG. 1, bio-oil 108 is produced using a fast pyrolysis process in pyrolyzer 104, where dry solid biomass is converted to liquid products using a reactor with high heat transfer rates, e.g., a fluidized bed reactor.

In the configuration shown in FIG. 1, biomass 102 can be fed to a pyrolyzer 104 where it is contacted with a circulating heat transfer medium, typically a fine, hot sand 106, resulting in high heating rates, on the order of 1000° C./sec. Average temperatures at the outlet of the pyrolyzer are ~500° C., with a typical residence time of less than two seconds. The biomass 102 undergoes thermal depolymerization of the lignin and cellulose molecules, resulting in a complex mixture of oxygenated organics following rapid cooling. In addition to the bio-oil produced, a gas 110 (comprising predominately CO, $CO_2$, and $H_2O$) and char can be formed. The char typically circulates with the sand 112 back to the combustor 140 where it provides the heat required to bring the sand back to the desired temperature for the pyrolyzer 104. In the configuration shown in FIG. 1, at least a portion of gas 110 is recycled 114 back to the pyrolyzer 104.

An example of a bio-oil 108 produced via a fast pyrolysis reactor similar to the configuration shown in FIG. 1 can be a complex mixture of oxygenated organics comprising predominately acids, aldehydes, ketones, phenolics, and alcohols. The composition varies with biomass source and processing. For example, the acids can be comprised predominately of formic (0.3-9.1 wt %) and acetic acid (0.5-12 wt %). The aldehydes can be comprised primarily of formaldehyde (0.1-3.3 wt %) and acetaldehyde (0.1-8.5 wt %). Other significant oxygenates can include phenol (0.1-3.8 wt %) and furfural alcohol (0.1-5.2 wt %). An example of such compositional data can be found in "Exploratory Studies of Fast Pyrolysis Oil Upgrading", F. H. Mahfud, Rijksuniversiteit Groningen, Nov. 16, 2007, ISBN 978-90-367-3226-9.

After leaving pyrolyzer 104, the bio-oil 108 can be mixed with a quench solvent 120. In the configuration shown in FIG. 1, quench solvent 120 corresponds to a portion of the effluent from hydrotreatment process 130, which is used to further reduce the oxygen content of bio-oil 108. It is noted that quench solvent 120 can also be beneficial as a solvent during hydrotreatment 130, as discussed further below. As an alternative to the configuration shown in FIG. 1, if quenching of the pyrolysis oil is not performed, solvent 120 can instead be recycled to mix with the input flow to the hydrotreatment reactor 130.

Figure 4:
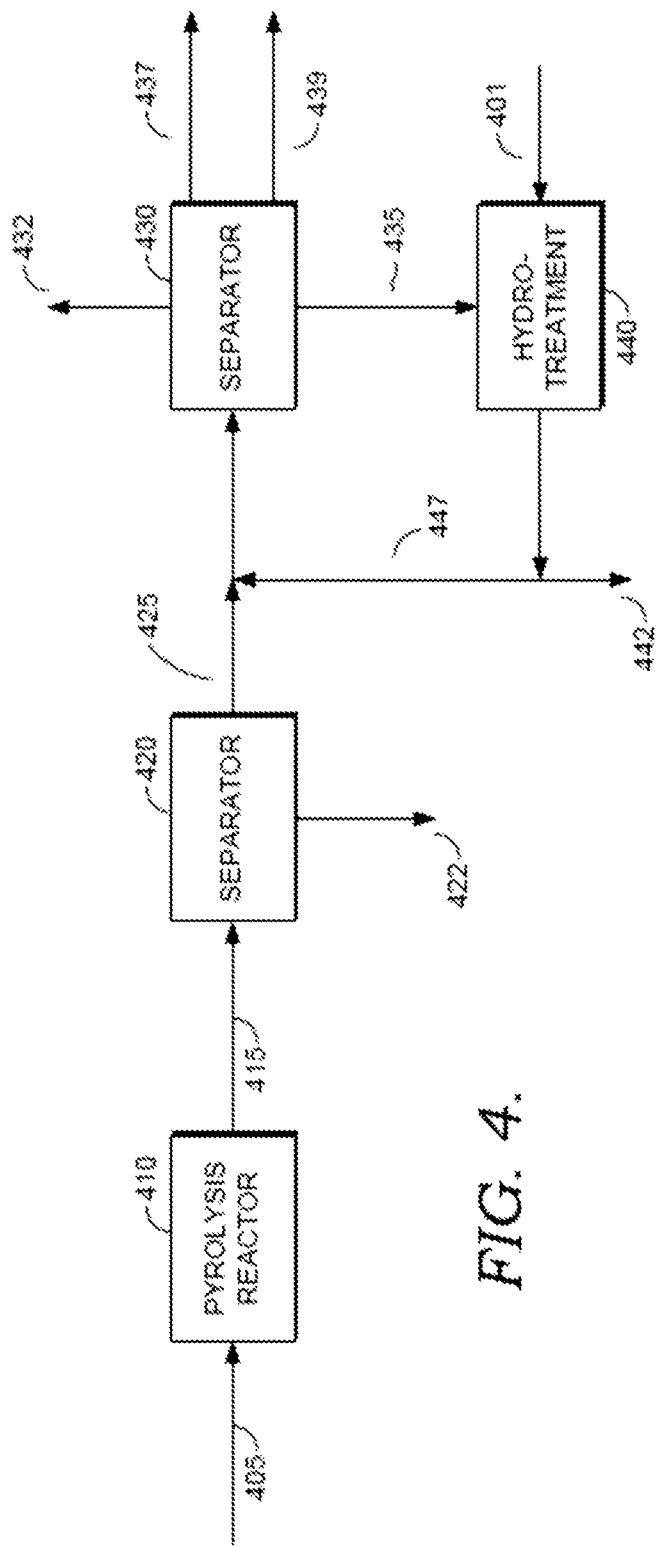
FIG. 4 schematically shows another example of a reaction system for mixing a pyrolysis effluent with a quench solvent.

FIG. 4 shows another example of a configuration for treating a lignin-containing feed. In FIG. 4, a feed including lignin-containing biomass is passed into a pyrolysis reactor 410. The hot pyrolysis effluent 415 is passed into a separator 420, where char, solids, and other heavy liquids 422 from the pyrolysis are separated from a hot gaseous effluent 425. Gaseous effluent 425 can be mixed with a quench fluid 447 that is formed from the effluent from hydrotreatment reactor 440. The mixture of gaseous effluent 425 and quench fluid 447 is then passed into separator 430. Due in part to mixing with the quench fluid 447, the temperature of gaseous effluent 425 can be reduced so that a portion of gaseous effluent 425 is condensed to a liquid phase. Separator 430 can separate any remaining gas phase products 432 from other liquid products, such as distillate fuel boiling range products 437, water and other aqueous products 439, and pyrolysis effluent 435 (which can also be referred to as a bio-oil). The pyrolysis effluent 435 can be hydrotreated 440 in the presence of a suitable hydrotreating catalyst and a hydrogen-containing gas 401 to form a hydrotreated or deoxygenated effluent. A portion of the deoxygenated effluent can be used as quench fluid 447 while another portion can be withdrawn as a deoxygenated or hydrotreated bio-oil product 442.

In this discussion, the terms "pyrolyze" and "pyrolyzing" are considered to be the act of converting a compound by pyrolysis. Pyrolysis is considered to be a chemical process in which a feed material is converted to one or more products by heat. By this definition, reactions that occur by heating in the presence of substantially reactive compounds (e.g., oxygen, hydrogen, sulfur-containing gases, and the like, but not including catalysts) to cause any significant degree of reaction involving (e.g., oxidation of) the feed material, such as by side reactions, are substantially excluded. The terms "thermolysis" or "thermal reaction" are considered to be synonyms for the term pyrolysis. According to the present invention, the term "torrefaction" is also considered as being within the definition of pyrolysis.

A wide range of feedstocks of various types, sizes, and moisture contents can be processed according to aspects of the present invention. Feedstocks that can be used in aspects of the present invention can comprise any hydrocarbon that can be thermally decomposed and/or transformed. Preferably, the feedstock comprises biomass, particularly biomass not typically processed or easily processable through chemical reactions. For example, the feedstocks can be comprised of at least 10 wt %, or at least 30 wt %, or at least 50 wt %, or at least 70 wt %, or at least 90 wt % biomass, based on total weight of feedstock that is processed or supplied to the thermal or pyrolysis reactor.

The term "biomass," for the purposes of the present invention, is considered any material not derived from fossil/mineral resources and comprising carbon, hydrogen, and oxygen. Examples of biomass can include, but are not limited to, plant and plant-derived material, algae and algae-derived material, vegetation, agricultural waste, forestry waste, wood waste, paper waste, animal-derived waste, poultry-derived waste, municipal solid waste, cellulose and cellulosics, carbohydrates or derivates thereof, charcoal, and the like, and combinations thereof. The feedstock can also comprise pyrolyzable components other than biomass, such as fossil/mineral fuels (e.g., coal, crude or refined petroleum feedstocks, and the like, as well as combinations thereof).

Additional or alternate examples of biomass that can be included as feedstock components include, but are not limited to, timber harvesting residues, softwood chips, hardwood chips, tree branches, tree stumps, leaves, bark, sawdust, off-spec paper pulp, corn, corn cob, corn stover, wheat straw, rice straw, sugarcane, bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, cloth, and combinations thereof.

Lignocellulose-comprising materials are also suitable for providing a lignin-comprising starting material for use in the process of the invention. Lignocellulose forms the structural skeleton of the cell walls of plants and comprises, as main constituents, lignin, hemicelluloses and cellulose. Further constituents of the cell walls of plants and therefore of lignocellulose-comprising materials obtained therefrom are, for example, silicates, extractable low molecular weight organic compounds (known as extractables, e.g., terpenes, resins, fats), polymers such as proteins, nucleic acids and plant gum (known as exsudate), etc.

Lignin is a biopolymer whose basic unit is essentially phenylpropane which, depending on the natural source, may be substituted by one or more methoxy groups on the phenyl rings and by a hydroxy group on the propyl units. Typical structural units of lignin are therefore p-hydroxyphenylpropane, guaiacylpropane and syringylpropane which are joined to one another by ether bonds and carbon-carbon bonds.

Suitable starting materials for the process of the invention include both lignocellulose-comprising materials which are used with their natural composition without further chemical treatment, and lignin-comprising streams from the processing of lignocellulose. In some aspects, a lignin-comprising stream can correspond to a stream produced from the digestion of a lignocellulose material for producing cellulose. The digestion makes possible an at least partial separation of the lignocellulose-comprising starting material into cellulose and materials accompanying cellulose, with lignin being among the latter.

The biomass to be pyrolyzed may be ground prior to pyrolyzing. For example, the biomass can be ground in a mill until a desired particle size is achieved. In one embodiment, the particle size of the biomass to be pyrolyzed can be sufficient (with or without grinding) to pass through a 30 mm screen, for example a 20 mm screen, a 10 mm screen, a 5 mm screen, or a 1 mm screen.

Pyrolysis can preferably be carried out in the presence of little to no oxygen. If oxygen is present, it can be present in an amount less than the stoichiometric amount required for complete combustion. Preferably, pyrolysis can be carried out in an environment (e.g., in the pyrolysis reactor) having an oxygen content of less than 40%, for example less than 30%, less than 20%, less than 10%, less than 5%, less than 1%, less than 0.5%, or less than 0.01% of the stoichiometric amount of oxygen required for complete combustion of the feedstock. In another preferred embodiment, pyrolysis can be carried out in the absence of any added oxygen (in which case oxygen may be present in trace amounts, but no oxygen is deliberately added).

Preferred pyrolysis conditions are typically those that minimize non-condensable gas formation and solid or char formation. Preferred conditions are also typically those that lead to condensable gas and liquid formation.

In one embodiment, pyrolyzed product can exit the pyrolysis reactor in the vapor phase. Preferably, the vapor phase can be passed through a filter to separate any solids from the more desirable product. The filtered vapors can then be condensed to form one or more liquid products. Preferably, condensation can be performed after mixing the filtered vapors with a suitable quench solvent. Condensation can be carried out using any equipment suitable for such purpose. For example, condensation can be carried out using a condensation train to collect the desired products. The condensation train can comprise at least one chilled water condenser, at least one electrostatic precipitator, or at least one coalescence filter, as well as combinations thereof.

The pyrolysis temperature can be sufficiently high to convert a sufficient quantity of feed to desired product, but not so high to produce undesired quantities of non-condensable gas or undesired solid. Preferably, feed can be pyrolyzed at a temperature from 200° C. to 600° C., for example from 300° C. to 600° C. or from 400° C. to 500° C. The pyrolysis pressure can be within a range that minimizes formation of non-condensable gas and solid product. The pressure can range from about 0 psig (about 0 kPag) to about 1000 psig (about 6.9 MPag), preferably from about 5 psig (about 35 kPag) to about 500 psig (about 3.5 MPag) or from about 10 psig (about 69 kPag) to about 200 psig (about 1.4 MPag).

Pyrolysis can generally be carried out for a time that enables a substantial quantity of feed to be converted into condensable vapor and/or liquid products. This can range over a wide period of time, depending upon pressure, temperature, and type of reactor used, inter alia. For example, pyrolysis can be carried out for a time from 0.1 second to 48 hours, for example, from 0.1 second to 24 hours or from 0.1 second to 1 hour. Shorter times are generally more preferred, such as from 0.1 second to 1 minute or from 0.1 second to 10 seconds. Thus, in some embodiments, fast pyrolysis can be used. Fast pyrolysis is a high-temperature process in which feedstock is rapidly heated. In some embodiments, the feedstock can be heated in the absence of oxygen. The feedstock can advantageously decompose to generate predominantly vapor and solid (char) products/by-products. The vapor product can preferably be cooled and condensed to form one or more liquid products. Multiple steps of heating and cooling can be carried out to produce intermediate pyrolysis liquid products. Fast pyrolysis processes can typically produce from about 60 wt % to about 75 wt % condensable gas and liquid products, from about 15 wt % to about 25 wt % solid char, and from about 10 wt % to about 20 wt % non-condensable gas products, but these relative numbers can depend heavily on the particular feedstock composition.

Slow pyrolysis can also be used. In slow pyrolysis, the feedstock can preferably be heated to not greater than about 600° C. for a time period ranging from 1 minute to 24 hours, preferably from 1 minute to 1 hour. Vapor product typically does not escape as rapidly in slow pyrolysis as in fast pyrolysis. Thus, vapor products may react with each other as solid char and liquid are being formed. Rates of heating in slow pyrolysis can typically be slower than in fast pyrolysis. A feedstock can be held at constant temperature or slowly heated. Vapors can be continuously removed as they are formed.

Vacuum pyrolysis can additionally or alternately be used. In vacuum pyrolysis, the feedstock is maintained at less than atmospheric pressure (i.e., below 0 psig or 0 kPag, but above 0 psia or 0 kPaa). Vacuum conditions can be used to decrease the boiling point, to avoid adverse chemical reactions, and to reduce the heating duty by using relatively lower temperatures.

Pyrolysis product can also contain water. As an example, condensed pyrolysis product can contain from 10 wt % to 30 wt % water. If desired, the water can be removed using any appropriate means, such as by flashing, decanting, distillation, membrane separation, or the like, or any combination thereof.

Any reactor suitable for pyrolyzing feedstock can be used in the process of aspects of the present invention. Examples of reactors can include, but are not limited to, auger reactors, ablative reactors, rotating cones, fluidized-bed reactors (e.g., circulating fluidized-bed reactors), entrained-flow reactors, vacuum moving-bed reactors, transport-bed reactors, fixed-bed reactors, microwave-assisted pyrolysis reactors, and the like, and combinations thereof in series and/or in parallel.

Processing of Lignin—Other Depolymerization Methods

In other aspects, other conventional methods can be used for depolymerization of lignin in a lignin-containing feed. Such conventional methods can include, for example, base catalyzed depolymerization. In a base catalyzed depolymerization, a lignin-containing feed can be dispersed in a basic solution, such as a 2-3 wt % aqueous solution of NaOH or another alkali hydroxide. The lignin-feed can be dispersed in the basic solution in a flow reactor or another convenient type of reactor.

The depolymerization reaction can be carried out at a temperature in the range of about 300° C. to about 340° C., and preferably in the range of about 310° C. to 330° C. A suitable liquid hourly space velocity (LHSV) of the lignin feed solution can be in the range of about 0.5 $h^{-1}$ to about 8 $h^{-1}$ can be selected in coordination with other processing variables, such as temperature.

Under suitable processing conditions, the depolymerization reaction proceeds with very high feed conversion (e.g., 85 wt % or greater), yielding a mixture of depolymerized lignin products. These products include mostly alkylated phenols such as mono-, di-, tri-, and polysubstituted phenols, accompanied by smaller variable amounts of alkylated alkoxyphenols, alkoxybenzenes, hydrocarbons, and oligomeric (incompletely depolymerized) compounds.

Hydrotreating and Solvent Assisted Hydrotreating for Depolymerization and/or Deoxygenation Still another option for depolymerizing a lignin-containing feed can be to hydrotreat the feed using a solvent assisted hydrotreating process. However, due in part to the elevated concentrations of oxygen in many feeds of biological origin, performing hydrotreatment on a bio-origin feed can create difficulties during conventional hydroprocessing. For example, oxygen heteroatoms in a hydrocarbonaceous feed can often be removed under relatively mild conditions. As a result, hydrotreating a feed with an elevated oxygen content can have the potential to generate a large amount of heat within a small region of a catalyst bed, as the oxygen-containing functional groups are readily removed under hydrotreating conditions. This excess heat can lead to additional coking of catalysts. Additionally, the high molecular weight of some bio-origin feeds can lead to difficulties in maintaining a desired flow pattern within a catalyst bed, which can also potentially lead to temperature control and coking problems.

Using a solvent as part of a hydrotreatment process for hydrotreating a bio-origin feed can reduce or minimize the difficulties noted above. Use of a solvent can reduce the viscosity of the overall feed, which can improve the flow of feed through a catalyst bed. A solvent can also serve as a non-reactive diluent in the hydrotreatment process, so that the amount of heat released within a catalyst bed is reduced due to a lower concentration of oxygen atoms in the combined feed corresponding to the bio-origin feed and the solvent.

In some aspects, the solvent assisted hydrotreating conditions can be selected to balance two different types of goals. One goal of the solvent assisted hydrotreating process can be to reduce the oxygen content of the feed to a desired level, such as less than about 3 wt % or less that about 1 wt %. It is noted that the "polymeric" linkages in a lignin compound typically correspond to chemical bonds involving oxygen atoms. As a result, hydrotreatment conditions that are suitable for deoxygenation of a feed and/or for hydrogenation of oxygen functional groups in a feed can also correspond to conditions suitable for depolymerization of lignin. Another goal of the solvent assisted hydrotreating process can be to reduce or minimize the amount of aromatic saturation that occurs during the hydrotreatment. Single ring aromatics in the hydrotreatment effluent are a potential source of raw material for formation of specialty chemicals such as para-xylene, so consuming hydrogen to saturate such aromatics is not preferred. These competing goals can be balanced by selecting suitable hydrotreating catalysts, such as catalysts including a non-noble Group VIII metal, and effective hydrotreating conditions.

In some aspects, the solvent component can correspond to a recycle stream of a portion of the liquid effluent or product generated from the hydroprocessing reaction. Optionally, in aspects where the hydrotreatment is performed on the effluent from a pyrolysis reaction zone, at least a portion of the solvent can correspond to a recycled portion of the hydroprocessing effluent used for quenching the pyrolysis oil. The recycle stream can be a portion of the total liquid effluent, or the recycle stream can include a portion of one or more distillation fractions of the liquid product from hydroprocessing. An example of a recycle stream corresponding to a portion of a distillation fraction is a recycle stream corresponding to a portion of the distillate boiling range product from hydroprocessing of the heavy feed.

The solvent and bio-oil (such as lignin-containing feed, depolymerized lignin-containing feed, or pyrolysis oil) can be combined so as to produce a combined feedstock to hydrotreatment that is comprised of from 10 wt % to 90 wt % of the bio-oil component and from 10 wt % to 90 wt % of the solvent component, based on total weight of the combined feed. Alternatively, the solvent and bio-oil can be combined so as to produce a combined feedstock that is comprised of from 30 wt % to 80 wt % of the bio-oil and from 20 wt % to 70 wt % of the solvent component, based on total weight of the combined feed. In some aspects, the solvent component is about 50 wt % or less of the combined feedstock, such as about 40 wt % or less or about 30 wt % or less. In other aspects where at least a portion of the solvent component corresponds to a recycled portion of the total liquid effluent, the solvent component can be greater than 50 wt % of the combined feedstock.

Another way of characterizing an amount of feedstock relative to an amount of solvent component, such as a recycle component, is as a ratio of solvent component to feedstock. For example, the ratio of solvent component to feedstock on a weight basis can be at least about 0.2, such as from about 0.3 to about 6.0, and preferably at least about 0.5 and/or less than about 5.0 or less than about 3.0.

The solvent can be combined with the bio-oil within the hydroprocessing vessel or hydroprocessing zone. Alternatively, the solvent and bio-oil can be supplied as separate streams and combined into one feed stream prior to entering the hydroprocessing vessel or hydroprocessing zone.

In still another option, instead of feeding a solvent component corresponding to a recycled portion of the total liquid effluent into a reactor from the reactor inlet, part of the solvent may be fed to the hydrotreatment reactor via inter-bed quench zones. This would allow the solvent to help control reaction exothermicity (adiabatic temperature rise) and improve the liquid flow distribution in the reactor bed.

Reactions for Oxygen Removal

Oxygen removal during hydroprocessing of a feedstock typically occurs via one of three reaction pathways. One potential reaction pathway is hydrodeoxygenation. In a hydrodeoxygenation reaction, oxygen is removed from feed molecule as water. The carbon chain for the feed molecule remains intact after a typical hydrodeoxygenation reaction. Water is a contaminant that can potentially contribute to deactivation of some hydrotreating catalysts, such as NiMo or CoMo type catalysts. However, by itself water does not lead to corrosion within a reaction system. Additionally, removing oxygen as water maintains the chain length of a feed molecule. Maintaining the chain length of molecules intended for use as a fuel or fuel blending product is usually beneficial, as it means that a greater percentage of the carbon from the feed is incorporated into the final fuel product.

Hydrodecarboxylation removes oxygen by forming $CO_2$ from biofeeds. This $CO_2$ forms carbonic acid when combined with water. Carbonic acid corrosion may require metallurgical upgrades to carbon steel in downstream equipment, particularly fin fans, heat exchangers, and other locations that liquid water will be present prior to a an amine scrubbing system or other system for removing $CO_2$.

Hydrodecarbonylation removes oxygen by forming CO from biofeeds. CO is a known inhibitor for hydrodesulfurization. For example, 1000 ppm CO can deactivate a conventional CoMo catalyst by 10%. CO is also not removed in appreciable quantities by conventional amine scrubbing systems. As such, CO can build up through gas recycle and can be cascaded to downstream hydrotreatment, dewaxing, and/or hydrofinishing stages. As a result, removing oxygen from a biocomponent feed as CO may require the use of pressure swing adsorbers (including rapid cycle pressure swing adsorbers) or other gas cleaning equipment in order to remove CO from a reaction system.

Depending on the conditions present in a reactor, the relative amounts of CO and $CO_2$ in a reactor can be modified by the water gas shift reaction. Additionally or alternately, a separate water gas shift stage can be used to modify the CO content of an effluent withdrawn from a reactor. The water gas shift reaction is an equilibrium reaction that can convert $CO_2$ and $H_2$ into CO and $H_2O$. Due to the water gas shift reaction, the amount of decarbonylation and decarboxylation may not be clear, due to conversion from one form of carbon oxide to another. Hydrodeoxygenation can be distinguished at least in part from decarbonylation and decarboxylation by characterizing the odd versus even numbered carbons in a deoxygenated product.

Most catalysts used for performing a catalytic deoxygenation of a bicomponent feed will be less than 100% selective for a given pathway. Instead, at least some deoxygenation of a feed will occur via each of the three pathways mentioned above during a typical catalytic deoxygenation of a feed. The relative amounts of deoxygenation by each method will vary depending on the nature of the catalyst and the reaction conditions.

Because feeds derived from biological sources typically have carbon chains with even numbers of carbon molecules, hydrodeoxygenation can be distinguished from decarbonylation and decarboxylation based on the carbon chain length of the resulting molecules. Hydrodeoxygenation typically leads to production of molecules with an even number of carbon atoms while decarbonylation and decarboxylation lead to molecules with an odd number of carbon atoms.

Processing Conditions for Deoxygenation

Deoxygenation of a feed by hydrotreating can be used on a variety of the initial or intermediate feed streams described herein, including (but not limited to) deoxygenation of a lignin-containing feed, deoxygenation of a depolymerized lignin-containing feed, or deoxygenation of a pyrolysis oil feed. Hydrotreating for deoxygenation of a feed can be performed on a feedstock with or without the presence of a solvent. As described above, one potential source of a solvent is a recycled portion of hydrotreated effluent. Another potential source of solvent is a quench solvent added after pyrolysis of a lignin-containing feed.

A catalyst suitable for oxygen removal during processing of an oxygen-containing feed can be a supported metal catalyst, such as a supported metal sulfide catalyst. The metal can be one or more Group VI metals (corresponding to Group 6 of the modern IUPAC periodic table) such as Mo or W, and/or one or more Group VIII non-noble metals (corresponding to Groups 8-10 of the modern IUPAC periodic table) such as Ni or Co. The support for the catalyst can be any convenient type of support, such as alumina, silica, zirconia, titania, amorphous carbon, or combinations thereof. One example of a suitable catalyst is a supported CoMo hydrotreating catalyst.

The catalysts used for hydrodeoxygenation can include conventional hydroprocessing catalysts, such as those that comprise at least one Group VIII non-noble metal (Columns 8-10 of IUPAC periodic table), preferably Fe, Co, and/or Ni, such as Co and/or Ni; and at least one Group VI metal (Column 6 of IUPAC periodic table), preferably Mo and/or W. Such hydroprocessing catalysts can optionally include transition metal sulfides. These metals or mixtures of metals are typically present as oxides or sulfides on refractory metal oxide supports. Suitable metal oxide supports include low acidic oxides such as silica, alumina, titania, zirconia, amorphous carbon, silica-titania, titania-alumina, and combinations thereof. Suitable aluminas are porous aluminas such as gamma or eta having average pore sizes from 50 to 200 Å, or 75 to 150 Å; a surface area from 100 to 300 $m^2/g$, or 150 to 250 $m^2/g$; and a pore volume of from 0.25 to 1.0 $cm^3/g$, or 0.35 to 0.8 $cm^3/g$. The supports are preferably not promoted with a halogen, such as fluorine, as this generally increases the acidity of the support.

The at least one Group VIII non-noble metal, in oxide form, can typically be present in an amount ranging from about 2 wt % to about 40 wt %, preferably from about 4 wt % to about 15 wt %. The at least one Group VI metal, in oxide form, can typically be present in an amount ranging from about 2 wt % to about 70 wt %, preferably for supported catalysts from about 6 wt % to about 40 wt % or from about 10 wt % to about 30 wt %. These weight percents are based on the total weight of the catalyst. Suitable metal catalysts include cobalt/molybdenum (1-10% Co as oxide, 10-40% Mo as oxide), nickel/molybdenum (1-10% Ni as oxide, 10-40% Co as oxide), or nickel/tungsten (1-10% Ni as oxide, 10-40% W as oxide) on alumina, silica, silica-alumina, zirconia, titania, or a combination thereof.

Alternatively, the hydrotreating catalyst can be a bulk metal catalyst, or a combination of stacked beds of supported and bulk metal catalyst. By bulk metal, it is meant that the catalysts are unsupported wherein the bulk catalyst particles comprise 30-100 wt % of at least one Group VIII non-noble metal and at least one Group VIB metal, based on the total weight of the bulk catalyst particles, calculated as metal oxides and wherein the bulk catalyst particles have a surface area of at least 10 $m^2/g$. It is furthermore preferred that the bulk metal hydrotreating catalysts used herein comprise about 50 to about 100 wt %, and even more preferably about 70 to about 100 wt %, of at least one Group VIII non-noble metal and at least one Group VIB metal, based on the total weight of the particles, calculated as metal oxides. The amount of Group VIB and Group VIII non-noble metals can easily be determined VIB TEM-EDX.

Typical effective conditions for processing a feedstock to remove oxygen can include conditions effective for hydrodeoxygenation, decarbonylation, and/or decarboxylation. A variety of conditions may be suitable as effective conditions. In some aspects, the effective conditions can correspond to effective conditions for hydrotreating a lignin-containing feed, a depolymerized lignin-containing feed, and/or a pyrolysis oil feed formed by quenching a gas-phase pyrolysis effluent as described herein. In such aspects, the pressure during processing of a feedstock for oxygen removal can correspond to a hydrogen partial pressure of about 200 psig (1.4 MPag) to about 700 psig (4.8 MPag). For example, the hydrogen partial pressure can be at least about 200 psig (1.4 MPag), or at least about 250 psig (1.7 MPag), or at least about 300 psig (2.1 MPag), or at least about 400 psig (2.8 MPag). Additionally or alternately, the hydrogen partial pressure can be about 700 psig (4.8 MPag) or less, such as about 600 psig (4.1 MPag) or less, or about 500 psig (3.4 MPag) or less, or about 450 psig or less (3.1 MPag). It is noted that for aspects where the hydroprocessing catalyst includes Ni, hydrogen partial pressures of about 500 psig (3.4 MPag) or less are preferred in order to avoid potential production of nickel carbonyl species. Lower hydrogen partial pressures are also beneficial for reducing or minimizing the amount of olefin saturation, including the amount of saturation from propylene to propane that occurs during deoxygenation.

In some alternative aspects, the effective conditions can be effective for hydrotreating a pyrolysis oil feed during solvent assisted hydrotreating of a pyrolysis oil feed. It is noted that this can include performing solvent assisted hydrotreating on a pyrolysis oil that is generated with or without the use of a quench solvent. The solvent assisted hydrotreating of the pyrolysis oil can be beneficial for converting oligomers in the pyrolysis oil into more valuable monomer type units. In such aspects, the pressure during processing of a feedstock for oxygen removal can correspond to a hydrogen partial pressure of about 400 psig (2.8 MPag) to about 1500 psig (10.3 MPag). For example, the hydrogen partial pressure can be at least about 400 psig (2.8 MPag), or at least about 500 psig (3.4 MPag), or at least about 600 psig (4.1 MPag), or at least about 800 psig (5.5 MPag). Additionally or alternately, the hydrogen partial pressure can be about 1500 psig (10.3 MPag) or less, such as about 1200 psig (8.2 MPag) or less, or about 1000 psig (6.9 MPag) or less, or about 900 psig or less (6.2 MPag). It is noted that for aspects where the hydroprocessing catalyst includes Ni, hydrogen partial pressures of about 500 psig (3.4 MPag) or less are preferred in order to avoid potential production of nickel carbonyl species. Lower hydrogen partial pressures are also beneficial for reducing or minimizing the amount of olefin saturation, including the amount of saturation from propylene to propane that occurs during deoxygenation.

The effective conditions for oxygen removal can also include a temperature, a hydrogen-containing treat gas rate, and a liquid hourly space velocity (LHSV). For example, for deoxygenation of a lignin-containing feed, a depolymerized lignin-containing feed, and/or a pyrolysis oil feed formed by quenching a gas-phase pyrolysis effluent as described herein, suitable effective temperatures can be from about 230° C. to about 375° C., such as at least about 250° C. or less than about 350° C. In other aspects, for deoxygenation of a pyrolysis oil feed (formed with or without the use of a quench solvent for the gas phase pyrolysis effluent), such as during solvent assisted hydrotreating of a pyrolysis oil feed, suitable effective temperatures can be from about 200° C. to about 450° C., such as at least about 250° C. or less than about 400° C. The LHSV can be from about 0.1 hr$^{-1}$ to about 10 hr$^{-1}$, such as from about 0.2 hr$^{-1}$ to about 5.0 hr$^{-1}$. The treat gas rate of hydrogen-containing can be any convenient value that provides sufficient hydrogen for deoxygenation of a feedstock. Typical values can range from about 500 scf/B (84 Nm$^3$/m$^3$) to about 10,000 scf/B (1685 Nm$^3$/m$^3$). Preferably, the hydrogen-containing gas can contain at least about 80 vol % of hydrogen, such as at least about 90 vol %. One option for selecting a treat gas rate can be to select a rate based on the expected stoichiometric amount of hydrogen for complete deoxygenation of the feedstock. For example, many types of biocomponent feeds have a stoichiometric hydrogen need for deoxygenation of between 200 scf/B (34 Nm$^3$/m$^3$) to about 1500 scf/B (253 Nm$^3$/m$^3$), depending on the mechanism for oxygen removal. In some aspects, the hydrogen treat gas rate can be selected based on a multiple of the stoichiometric hydrogen need, such as at least about 1 times the hydrogen need, or at least about 1.5 times the hydrogen need, or at least about 2 times the hydrogen need. In other aspects where at least a portion of the gas phase deoxygenation effluent is recycled, any convenient amount of hydrogen relative to the stoichiometric need can be used.

In some aspects, an additional consideration during deoxygenation can be maintaining the sulfided state of the catalyst for catalysts that include sulfide metals. If little or no sulfur is present in the reaction environment, the sulfided metal on the catalyst will have a tendency to be reduced and/or converted to oxide form, leading to reduced deoxygenation activity for the catalyst. To maintain catalyst activity, some sulfur can be introduced into the reaction environment. The sulfur can be introduced as sulfur in a mineral feed that is blended with the triglyceride-containing biocomponent feed. Additionally or alternately, sulfur can be introduced as part of the gas phase environment, such as by using an H$_2$ source that contains some H$_2$S. The amount of sulfur present in the reaction environment can be at least about 100 wppm, such as at least about 200 wppm or at least about 500 wppm. If this sulfur is introduced as a gas phase component (such as H$_2$S), the sulfur can be easily removed from any liquid products using a gas-liquid separation. If the sulfur is introduced as part of the feed, it may be feasible to blend the resulting products to achieve an acceptable sulfur level in any final product. Alternatively, subsequent hydroprocessing can be used to reduce the sulfur level of the products, if olefin preservation is not desired.

The effective conditions for deoxygenation can be suitable for reducing the oxygen content of the feed to less than about 1.0 wt %, such as less than about 0.5 wt % or less than about 0.2 wt %. Although the stoichiometric hydrogen need is calculated based on complete deoxygenation, reducing the oxygen content to substantially zero is typically not required to allow further processing of the deoxygenated feed in conventional equipment. Alternatively, in some aspects the effective conditions can be selected to perform at least a partial deoxygenation of the feedstock. A partial deoxygenation corresponds to conditions suitable for reducing the oxygen content of the feed by at least about 40%, such as by at least about 50% or at least about 75%.

The effective deoxygenation conditions, including the catalyst, can be selected to allow for a desired amount of deoxygenation while also preserving aromatic compounds present in the feed. In various aspects, the amount of aromatic compounds present in a deoxygenated feed can be at least 20 wt % of the deoxygenated feed, such as at least about 25 wt %, or at least about 35 wt %, or at least about 50 wt %. Of course, the amount of aromatic compounds present in a feed will typically not increase after deoxygenation, so achieving the desired amount of aromatic compounds in a deoxygenated feed is dependent in part on the aromatics content prior to deoxygenation.

Dealkylation and Alkylation (Xylene Formation)

After depolymerization of a lignin containing feed, a variety of monolignol compounds can be formed. Examples of monolignols that can form during depolymerization of lignin include coumaryl alcohol, coniferyl alcohol, and sinapyl alcohol. These monolignol compounds include an aromatic ring and at least one side chain containing multiple carbons, such as at least 3 carbons.

Depending on the nature of the depolymerization method, deoxygenation of the lignin-containing feed can occur during the same process and/or deoxygenation can be performed as a subsequent process. After deoxygenation and optional saturation of vinyl groups, at least a portion of the products from depolymerization and deoxygenation of lignin can correspond to alkylated benzenes, such as n-propyl benzene. Alkylated benzenes can be valuable products without further processing. Alternatively, it may be desirable to convert the alkylated benzenes into desired products, such as p-xylene. This can be achieved by dealkylating the alkylated benzenes and then using the benzenes to form desired aromatics, such as toluene or p-xylene.

In a dealkylation process, aromatic products are at least partly transformed by action of hydrogen and/or water vapor so that substituents are replaced by hydrogen. This can correspond to hydrodealkylation or steam dealkylation. The dealkylation can be performed in the presence of a catalyst, such as a catalyst containing a molecular sieve as described below in association with alkylation processes. Other examples of suitable dealkylation catalysts can include catalysts containing a molecular sieve such as ZSM-5, ZSM-11, ZSM-12, ZSM-35, and ZSM-38. Suitable dealkylation catalysts can further include a metal with hydrogenation/dehydrogenation activity, such as a metal selected from groups 8-11 of the IUPAC periodic table. It is noted that hydroxyl or alkoxy groups still present as substituents on an aromatic ring can also be removed under the dealkylation conditions described herein.

In the case of a hydrodealkylation in the context of the invention, molecular hydrogen (in pure form or in admixture with other components, such as CO), is fed into the dealkylation zone in addition to the alkylated aromatics derived from the lignin-containing feed. In the case of a steam dealkylation in the context of the invention, water (in pure form or in admixture with other components), is fed into the dealkylation zone in addition to the alkylated aromatics derived from the lignin-containing feed. The dealkylation process can also be configured as a mixed form of hydrodealkylation and steam dealkylation. Both water and molecular hydrogen are then fed into the dealkylation zone in addition to the alkylated aromatics derived from the lignin-containing feed.

The temperature in the dealkylation zone is preferably in the range from 400° C. to 900° C., such as from 500° C. to 800° C. or from 400° C. to 600° C. The absolute pressure in the dealkylation zone is preferably in the range from 1 bar (0.1 MPa) to 100 bar (10 MPa), such as from 1 bar (0.1 MPa) to 20 bar (2.0 MPa), or from 1 bar (0.1 MPa) to 10 bar (1.0 MPa). In aspects where $H_2$ is supplied to the dealkylation process, the ratio of the amount of $H_2$ used to $H_2$ (stoichiometric) in the hydrodealkylation is preferably in the range from 0.02 to 50, particularly preferably from 0.2 to 10. Here, $H_2$ (stoichiometric) is the amount of $H_2$ is theoretically required for complete conversion of the aromatics fed into the dealkylation zone into benzene, with the assumption that 1 mol of $H_2$ reacts per ring substituent. The residence time in the dealkylation zone can be from 0.1 s to 500 s, such as from 0.5 s to 200 s.

The dealkylated aromatics from the dealkylation process can then be used for formation of other aromatics, such as para-xylene. One known route for the manufacture of para-xylene is by the methylation of benzene and/or toluene. For example, U.S. Pat. No. 8,344,197 discloses a process for the selective production of para-xylene.

An important parameter in the reaction of benzene and/or toluene with methanol to produce para-xylene is temperature, with relatively high temperatures, typically between 450° C. and 700° C., being required to maximize conversion. As a result, the aromatic and methanol feeds are preheated before being supplied to the alkylation reactor(s), with the exothermic heat generated by the alkylation reaction generally being sufficient to maintain the reaction temperature at the desired value. In practice, however, there are limits on the temperatures to which the different feeds can be preheated. For example, in the case of the benzene/toluene feed, the preheating temperature is limited by the coking rates in the preheater which, depending on factors such as heat flux, stream composition and heat transfer surface metallurgy, will generally be about 550° C. In the case of the methanol feed, decomposition to carbon oxides, hydrogen and methane will generally limit the preheating temperature to about 220° C.

Generally, the conditions employed in an alkylation process can include a temperature between about 450° C. and about 700° C., such as between about 550° C. and about 650° C.; a pressure between about 1 atmosphere and about 1000 psig (between about 100 kPa and about 7000 kPa), such as between about 10 psig and about 200 psig (between about 170 kPa and about 1480 kPa); a molar ratio of aromatic to methanol in the reactor charge of at least about 0.2, and preferably from about 2 to about 20; and a weight hourly space velocity ("WHSV") for total hydrocarbon feed to the reactor(s) of about 0.2 to about 1000, preferably about 0.5 to about 500 for the aromatic reactant, and about 0.01 to about 100 for the methanol reagent, based on total catalyst in the reactor(s).

More specifically, the conditions in the alkylation process can be controlled so as to maximize the selectivity of the reaction to the desired para-xylene product. In general, this is achieved by maintaining the reaction temperature at a relatively high value (about 590° C.) and operating with an excess of the aromatic reagent (a molar ratio of aromatic to methanol in the reactor charge of at least 2). Normally, the alkylation conditions are substantially adiabatic, that is, heat is not actively added to or removed from the alkylation reactor system. Thus, all the heat required to maintain the reaction temperature at the desired value is provided by a combination of the heat initially supplied to the methanol and aromatic feeds and the exothermic heat generated in the reaction. In particular, the temperature control in the present process involves initially preheating the methanol and aromatic feeds to first and second predetermined temperatures, respectively, at or near the maximum values consistent with avoiding feed decomposition in the preheaters. In the case of the methanol feed, this involves preheating the feed to a first temperature between about 150° C. and about 300° C., such as about 220° C., whereas in the case of the aromatic feed the second temperature is between about 300° C. and about 700° C., such as about 550° C.

In addition, temperature control is effected by measuring the temperature in the alkylation reactor and comparing the measured temperature with a predetermined optimal temperature in the reactor (usually about 590° C.). The molar ratio of methanol to aromatic feedstock supplied to the reactor is then used to reduce any difference between the measured and predetermined optimal temperatures in the reactor, generally to a value to less than 10° C., typically to less than 5° C. Thus, since the conversion of methanol in the process, whether by alkylation or the production of light gases, is exothermic, any increase in the methanol to aromatic molar ratio will increase the supply of heat to the reaction and hence, raise the reaction temperature. Alternatively, since conversion of methanol is the rate limiting step, any decrease in the methanol to aromatic molar ratio will decrease the supply of heat to the reaction and hence lower the reaction temperature. Controlling the reaction temperature in this manner guarantees that, for a given desired reaction temperature and maximum value of the feed preheating temperatures, the lowest possible methanol to aromatic molar ratio will be employed. This maintains the methanol concentration in the reactor at its lowest possible value, resulting in the highest possible selectivity to the desired xylene product.

For an adiabatic system, if the reactor is perfectly mixed, the temperature will be uniform throughout the reactor and all reactions will proceed at a single reaction temperature. Thus, in effecting temperature control, it is unimportant where the temperature in the reactor is measured. On the other hand, if the reactor is not perfectly mixed, or is plug flow, there will be a temperature profile across the reactor, with the highest temperature being at the reactor outlet. In this case, the reactor temperature is preferably measured at or near the point where the reaction effluent exits the reactor.

In one embodiment of the present process, the degree of conversion of methanol is also controlled so as to remain substantially constant. This can be achieved without disturbing the reaction temperature control by adjusting the amount of catalyst in the reactor, the catalyst activity or both. Adjustment of catalyst amount and activity are easiest to effect in a fluid bed system as described above. Thus, for example, the catalyst amount can be adjusted by adding or removing catalyst from the reactor, or by shifting the amount of catalyst in the reactor versus that in the regenerator, whereas the catalyst activity can be adjusted by changing either or both of the catalyst regeneration rate and the make-up rate of fresh catalyst.

In addition to paraxylene, the process according to the present invention can be used to produce toluene (from benzene), other C7+ products such as ortho- and metaxylene, along with side products including light olefins such as ethylene, propylene, butylene isomers, pentene, hydrogen, methane, ethane, butane, pentane, butadiene, and the like. Accordingly, while the present invention is directed most specifically to the preferred embodiment of the production of paraxylene, one of skill in the art would recognize that through routine experimentation the process of the invention can be optimized for the production of one of the other products set forth herein.

The alkylation process employed herein can employ any aromatic feedstock comprising toluene and/or benzene, although in general it is preferred that the aromatic feed contains at least 90 weight %, especially at least 99 weight %, of benzene, toluene or a mixture thereof. An aromatic feed containing at least 99 weight % toluene is particularly desirable. Similarly, although the composition of the methanol-containing feed is not critical, it is generally desirable to employ feeds containing at least 90 weight %, especially at least 99 weight %, of methanol.

The catalyst employed in the present process is a porous crystalline material. The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof are taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites may have Diffusion Parameter values in excess of the 0.1-15 sec$^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is derived by measuring the n-hexane adsorption capacity of the zeolite, before and after steaming, at 90° C. and 75 ton n-hexane pressure.

Steaming of the porous crystalline material is effected at a temperature of at least about 950° C., preferably about 950° C. to about 1075° C., and most preferably about 1000° C. to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB, and VIA of the Periodic Table (IUPAC version). Most preferably, said at least one oxide modifier is selected from oxides of boron, magnesium, calcium, lanthanum and most preferably phosphorus. In some cases, it may be desirable to combine the porous crystalline material with more than one oxide modifier, for example, a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, and preferably is between about 0.1 and about 10 wt %, based on the weight of the final catalyst.

The porous crystalline material employed in the present process may be combined with a variety of binder or matrix materials resistant to the temperatures and other conditions employed in the process. Such materials include active and inactive materials such as clays, silica and/or metal oxides such as alumina. The latter may be either naturally occurring, or in the form of gelatinous precipitates, or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. The relative proportions of porous crystalline material and inorganic oxide matrix vary widely, with the content of the former ranging from about 1 to about 90% by weight and more usually, particularly when the composite is prepared in the form of beads, in the range of about 2 wt % to about 80 wt % of the composite.

The alkylation process can be conducted with the catalyst disposed in one or more fixed, moving or fluidized beds. Preferably, however, the catalyst particles are disposed in one or more fluidized beds. Each of the methanol and aromatic feeds can be injected into the fluidized catalyst in a single stage. However, in a preferred embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced fluidized catalyst beds, with the aromatic feed being injected into a lower portion of the first fluidized bed and part of the methanol being injected into an intermediate portion of the first bed and part of the methanol being injected into or between adjacent downstream catalyst beds.

Irrespective of the disposition of the catalyst, as the alkylation reaction proceeds, the catalyst gradually deactivates as a result of build-up of carbonaceous material, generally referred to as "coke" on the catalyst. Thus, a portion of the catalyst in the or each alkylation reactor is generally withdrawn, either on a continuous or a periodic basis, and fed to a separate regenerator. In the regenerator, the catalyst, again preferably in the form of a fluidized bed, is contacted with an oxygen-containing gas, such as air, at a temperature between about 400° C. and about 700° C. so as to burn off the coke and regenerate the catalyst. The regenerated catalyst is then continuously or periodically returned to the alkylation reactor.

Although the present invention has been described in terms of specific embodiments, it is not so limited. Suitable alterations/modifications for operation under specific conditions should be apparent to those skilled in the art. It is, therefore, intended that the following claims be interpreted as covering all such alterations/modifications as fall within the true spirit/scope of the invention.

What is claimed is:

1. A method of converting lignin to aromatic compounds, comprising:
    processing a lignin-containing feed under effective depolymerization conditions to form a depolymerized effluent containing monolignols;
    mixing the depolymerized effluent with a solvent, wherein the solvent is in a liquid phase, has a T5 boiling point of at least about 240° C. and comprises at least about 50 wt % aromatic compounds; and
    exposing at least a portion of the depolymerized effluent and solvent to a deoxygenation catalyst under effective deoxygenation conditions to form at least a deoxygenated effluent,
    wherein the solvent comprises a recycled portion of the deoxygenated effluent.

2. The method of claim 1, wherein processing a lignin-containing feed under effective depolymerization conditions comprises processing the lignin-containing feed under effective pyrolysis conditions in a pyrolysis reaction zone to form a pyrolysis effluent, the pyrolysis effluent exiting the pyrolysis reaction zone at an exit temperature.

3. The method of claim 2, wherein mixing the depolymerized effluent with the solvent comprises:
    mixing the pyrolysis effluent with a quench solvent, the quench solvent being at a quench solvent temperature and the pyrolysis effluent being at a mixing temperature that is less than about 100° C. different than the exit temperature; and
    forming a liquid product comprising at least a portion of the pyrolysis effluent and the quench solvent, the weight ratio of quench solvent to pyrolysis oil effluent in the liquid product being at least about 1:1.

4. The method of claim 3, wherein the quench solvent temperature is different from the mixing temperature of the pyrolysis effluent by about 100° C. or less.

5. The method of claim 3, wherein the quench solvent temperature is different from the mixing temperature of the pyrolysis effluent by more than about 100° C.

6. The method of claim 5, wherein the quench solvent is a liquid at the quench solvent temperature.

7. The method of claim 3, wherein the quench solvent comprises about 5 wt % or less of compounds containing vinyl or allylic functional groups.

8. The method of any one of claims 1-4, 5, 6 or 7 wherein the deoxygenated effluent has an oxygen content of about 1 wt % or less.

9. The method of claim 8, wherein the effective deoxygenation conditions comprise a temperature of about 200° C. to about 450° C. and a hydrogen partial pressure of about 400 psig to about 1500 psig.

10. The method of claim 1, further comprising exposing at least a portion of the deoxygenated effluent to a dealkylation catalyst under effective dealkylation conditions to form benzene.

11. The method of claim 10, further comprising exposing at least a portion of the benzene to an alkylation catalyst and methanol under effective alkylation conditions to form xylene.

12. A method of converting lignin to aromatic compounds, comprising:
    processing a lignin-containing feed under effective depolymerization conditions to form a depolymerized effluent containing monolignols;
    mixing the depolymerized effluent with a solvent, wherein each of the depolymerized effluent and the solvent are in the gas phase, the solvent has a T5 boiling point of at least about 240° C. and comprises at least about 50 wt % of aromatic compounds;
    exposing at least a portion of the depolymerized effluent containing monolignols and the solvent to a deoxygenation catalyst under effective deoxygenation conditions to form a deoxygenated effluent containing alkylated benzene compounds;
    exposing at least a portion of the alkylated benzene compounds to a dealkylation catalyst under effective dealkylation conditions to form benzene; and
    exposing at least a portion of the benzene to an alkylation catalyst and methanol under effective alkylation conditions to form xylene,
    wherein the solvent comprises a recycled portion of the deoxygenated effluent.

13. The method of claim 12, wherein the effective depolymerization conditions comprise pyrolysis conditions, the depolymerized effluent containing monolignols comprising a pyrolysis effluent.

14. The method of claim 13, wherein the mixing is performed with the solvent being at a solvent temperature and the pyrolysis effluent being at a temperature that is less than about 100° C. different than a temperature of the pyrolysis effluent when exiting a pyrolysis reaction zone.

15. A method of converting lignin to aromatic compounds, comprising:
    processing a lignin-containing feed under effective pyrolysis conditions to form a pyrolysis effluent containing monolignols;
    mixing the pyrolysis effluent with a quench solvent, wherein the quench solvent is in a liquid phase, has a T5 boiling point of at least about 240° C. and comprises at least about 50 wt % of aromatic compounds; and exposing at least a portion of the depolymerized effluent and quench solvent to a deoxygenation catalyst under effective deoxygenation conditions to form at least a deoxygenated effluent,
wherein a quench solvent temperature is different from a mixing temperature of the pyrolysis effluent by about 100° C. or less.

* * * * *